US007531622B2

(12) United States Patent
Dumy et al.

(10) Patent No.: US 7,531,622 B2
(45) Date of Patent: May 12, 2009

(54) SYNTHESIS AND CHARACTERIZATION OF NOVEL SYSTEMS FOR GUIDANCE AND VECTORIZATION OF MOLECULES OF THERAPEUTIC INTEREST TOWARDS TARGET CELLS

(75) Inventors: Pascal Dumy, Allevard (FR); Marie-Christine Favrot, Corenc (FR); Didier Boturyn, Grenoble (FR); Jean-Luc Coll, Claix (FR)

(73) Assignees: Centre National de la Recherche Scientifique- CNRS (FR); Universite Joseph Fourier (FR); Inserm (FR)

( * ) Notice: Subject to any disclaimer, the term of this patent is extended or adjusted under 35 U.S.C. 154(b) by 0 days.

(21) Appl. No.: 10/528,320

(22) PCT Filed: Sep. 19, 2003

(86) PCT No.: PCT/FR03/02773

§ 371 (c)(1),
(2), (4) Date: Oct. 11, 2005

(87) PCT Pub. No.: WO2004/026894

PCT Pub. Date: Apr. 1, 2004

(65) Prior Publication Data

US 2006/0173160 A1    Aug. 3, 2006

Related U.S. Application Data

(60) Provisional application No. 60/411,845, filed on Sep. 19, 2002.

(30) Foreign Application Priority Data

Sep. 19, 2002  (FR)  .................................. 02 11614

(51) Int. Cl.
*C07K 7/50* (2006.01)
(52) U.S. Cl. ........................ 530/317; 530/345; 530/329; 530/330; 514/9
(58) Field of Classification Search ................. 530/317, 530/345, 329, 330; 514/9
See application file for complete search history.

(56) References Cited

U.S. PATENT DOCUMENTS

2003/0125243 A1* 7/2003 Liu et al. ........................ 514/9

FOREIGN PATENT DOCUMENTS

WO    WO 99/58162    * 11/1999

OTHER PUBLICATIONS

Kantlehner M. et al. "Selective RGD-Mediated Adhesion of Osteoblasts at Surfaces of Implants" 1999, Angew. Che. Int. Ed. vol. 38, pp. 560-562.*

Scheibler L. et al. "Functional Molecular Thin Films: Topological Templates for the Chemoselective Ligation of Antigenic Peptides to Self-Assembled Monolayers" 1999, Angew. Chem. Int. Ed. vol. 38, pp. 696-699.*

Pascal Dumy et al., A Convenient Synthesis of Cyclic Peptides as Regioselectively Addressable Functionalized Templates (RAFT), *Tetrahedron Letters*, vol. 36, No. 8, pp. 1255-1258, 1995.

Francesco Peri et al., Chemo- and Stereoselective Glycosylation of Hydroxylamino Derivatives: A Versatile Approach to Glycoconjugates, *Tetrahedron*, vol. 54, pp. 12269-12278, 1998.

Olivier Renaudet et al., Expedient synthesis of aminooxylated-carbohydrates for chemoselective access of glycoconjugates, *Tetrahedron Letters*, vol. 42, pp. 7575-7578, 2001.

Damien Forget et al., 3'-Oligonucleotides conjugation via chemoselective oxime bond formation, *Tetrahedron Letters*, vol. 42, No. 52, pp. 9171-9174, 2001.

Olivier Renaudet et al., Chemoselectively Template-Assembled Glycoconjugates as Mimics for Multivalent Presentation of Carbohydrates, *Organic Letters*, vol. 5, No. 3, pp. 243-246, 2003.

Lemieux et al., "Chemoselective Ligation Reactions with Proteins, Oligosaccharides and Cells," *Trends in Biotechnology*, Dec. 1998, vol. 16, pp. 506-513.

Tam et al., "Chemoselective Approaches to the Preparation of Peptide Dendrimers and Branched Artificial Proteins Using Unprotected Peptides as Building Blocks," *Biomedical Peptides, Proteins & Nucleic Acids*, 1995, vol. 1, pp. 123-132.

Maynard et al., "Inhibition of Cell Adhesion to Fibronectin by Oligopeptide-Substituted Polynorbomenes," *J. Am. Chem. Soc.*, Jan. 26, 2001, vol. 123, pp. 1275-1279.

Scheibler et al., "Functional Molecular Thin Films Topological Templates for the Chemoselective Ligation of Antigenic Peptides to Self-Assembled Monolayers," *Agnew. Chem. Int. Ed.*, 1999, vol. 38, No. 5, pp. 696-699.

Brooks, P.C. et al., "Requirement of Vascular Integrin alpha$_v$ beta$_3$ for Angiogenesis," *Science*, Apr. 22, 1994, vol. 264(5158), pp. 569-571.

Bettahi, I. et al., "Antitumor Activity of a Self-Adjuvanting Glyco-Lipopeptide Vaccine Bearing B Cell, CD4* and CD8* T Cell Epitopes," *Cancer Immunol Immunother*, © Springer-Verlag 2008, 14 pages.

Foillard, S. et al., "Synthesis and Biological Charcterisation of Targeted Pro-Apoptotic Peptide," *ChemBioChem*, 2008, vol. 9, 2326-2332.

(Continued)

*Primary Examiner*—David Lukton
(74) *Attorney, Agent, or Firm*—DLA Piper LLP (US)

(57) ABSTRACT

A method for preparing a grafted homodetic cyclopeptide forming a framework that defines a grafted upper face and grafted lower face, including synthesizing a linear peptide from modified or unmodified amino acids, some of which carry orthogonal protective groups; intramolecular cyclizing the resulting protected linear peptide; substituting some or all of orthogonal protective groups with a protected precursor; and grafting at least one molecule of interest onto one and/or the other face of the framework via an oxime bond.

31 Claims, 9 Drawing Sheets

OTHER PUBLICATIONS

Kuphal, S. et al., "Integrin Signaling in Malignant Melanoma," *Cancer and Metastasis Reviews*, 2005, vol. 24, pp. 195-222.

Murphy, E.A. et al., "Nanoparticle-Mediated Drug Delivery to Tumor Vasculature Suppresses Metastasis," *PNAS*, Jul. 8, 2008, vol. 105, No. 27, pp. 9343-9348.

Sancey, L. et al., "In Vivo Imaging of Tumour Angiogenesis in Mice with the $\alpha_v\beta_3$ Integrin-Targeted Tracer $^{99m}$Tc-RAFT-RGD," *Eur J Nucl Med Mol Imaging*, 2007, vol. 34, pp. 2037-2047.

* cited by examiner

Reagents : a) AcONH$_4$ 0.1M pH4, 50-65% ; b) NaIO$_4$, water, 61% ; c) AcONa 0.1M, pH4, 50-70%.

(a) NaIO$_4$
(b) H$_2$NO-R$_1$
(c) R$_2$-SH
(d) R$_1$CHO

SEQUENCE LISTING

```
<160> NUMBER OF SEQ ID NOS: 5

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: PEPTIDE
<222> LOCATION: (1)..(5)
<223> OTHER INFORMATION: Circular peptide in which the Phe in position
      4 is the D-isomer

<400> SEQUENCE: 1

Arg Gly Asp Phe Lys
```

```
                   1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: PEPTIDE
<222> LOCATION: (1)..(5)
<223> OTHER INFORMATION: Circular peptide in which the Tyr in position
      4 is the D-isomer

<400> SEQUENCE: 2

Arg Gly Asp Tyr Lys
 1               5

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      apotogenic peptide

<400> SEQUENCE: 3

Lys Leu Ala Lys Lys Leu Ala Lys
 1               5

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: PEPTIDE
<222> LOCATION: (1)..(10)
<223> OTHER INFORMATION: Circular peptide

<400> SEQUENCE: 4

Pro Gly Lys Lys Lys Pro Gly Lys Lys Lys
 1               5                  10

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Asn, Gln, Lys, Arg, His, Cys, Asp or Glu
<220> FEATURE:
<221> NAME/KEY: MOD_RES
<222> LOCATION: (9)
<223> OTHER INFORMATION: Asn, Gln, Lys, Arg, His, Cys, Asp or Glu
<220> FEATURE:
<221> NAME/KEY: PEPTIDE
<222> LOCATION: (1)..(10)
<223> OTHER INFORMATION: Circular peptide

<400> SEQUENCE: 5

Pro Gly Lys Xaa Lys Pro Gly Lys Xaa Lys
 1               5                  10
```

SYNTHESIS AND CHARACTERIZATION OF NOVEL SYSTEMS FOR GUIDANCE AND VECTORIZATION OF MOLECULES OF THERAPEUTIC INTEREST TOWARDS TARGET CELLS

RELATED APPLICATION

This is a §371 of International Application No. PCT/FR2003/002773, with an international filing date of Sep. 19, 2003 (WO 2004/026894, published Apr. 1, 2004), which is based on French Patent Application No. 02/11614, filed Sep. 19, 2002, and U.S. Patent Application No. 60/411,845, filed Sep. 19, 2002.

FIELD OF THE INVENTION invention relates the synthesis and characterization of new systems for guiding and vectoring molecules of therapeutic interest toward target cells. More particularly, the invention relates to molecular complexes capable of combining several functional molecules possessing predefined recognition properties or effective properties with the process for preparing them, and with their therapeutic use or use as diagnostic tools.

BACKGROUND

The literature describes a number of methods for obtaining monovalent polyfunctional bioconjugated complexes (Lemieux et al. *Trends in Biotechnology*, 1998, 16, 506-513). These complexes evoke a relatively weak biological response, however. Multivalent systems were then prepared (Tam et al., *Biomedical Peptides, Proteins & Nucleic Acids*, 1995, 1, 123-132). Studies demonstrated that polyvalent complexes were, in general, much better biological tools than monovalent bioconjugated complexes (Grubbs, R. H. et al., *J. Am. Chem. Soc.*, 2001, 123, 1275-1279).

The significance of such bioconjugated complexes is that they combine the properties characteristic of at least two different classes of molecules. One of the difficulties that arises, however, is the potential interaction that the various molecules of a bioconjugate can exhibit. That interaction can modify the properties resulting from bioconjugation. One solution to that problem is to spatially separate the bioconjugation points, which has led to the development of addressable molecular templates or frameworks. L. Scheibler, P. Dumy et al., *Tetrahedron*, 1998, 54, 3725-3734, disclose the synthesis and characterization of molecular frameworks functionalized with coordination groups and alkane chains.

Attaching the molecules of interest to the framework presents another difficulty. L. Scheibler, P. Dumy et al., *Angew. Chem. Int. Ed.*, 1999, 38, 696-699, disclose a framework that has been chemoselectively functionalized on one face by means of an oxime bond.

The existing art does not, however, teach how to synthesize a framework functionalized on both faces, at least one of the functionalizations being chemoselective, and each face carrying molecules of therapeutic or diagnostic or labeling interest.

It would therefore be advantageous to provide a method for preparing a homodetic cyclopeptide grafted on both of its faces.

SUMMARY OF THE INVENTION

This invention relates to a method for preparing a grafted homodetic cyclopeptide forming a framework that defines a grafted upper face and a grafted lower face including synthesizing a linear peptide from modified or unmodified amino acids, some of which carry orthogonal protective groups, intramolecular cyclizing the resulting protected linear peptide, substituting some or all of orthogonal protective groups with a protected precursor, grafting at least one molecule of interest onto one and/or the other face of the framework via an oxime bond.

This invention also relates to the grafted homodetic cyclopeptide obtained by the method grafted on one of its faces with carbohydrate derivatives and on the other face of the framework with one or several chromophore(s), one or several biotin(s), one or several fluorophores(s), one or several radioemitter(s), or a chemical precursor group or ligand.

This invention further relates to a therapeutic or diagnostic composition including the grafted homodetic cyclopeptide.

This invention still further relates to a method of treating cancer including administering a therapeutically effective amount of the therapeutic or diagnostic composition to a patient.

This invention also further relates to a method of treatment cancer including administering a therapeutically effective amount of the therapeutic or diagnostic composition for the suppression of neoangiogenesis.

BRIEF DESCRIPTION OF THE DRAWINGS

Other aspects of the framework and of its grafting according to the present invention are presented in the detailed description below, which should be read with reference to the Figures and illustrates the invention in non-limiting fashion.

FIG. 2a discloses SEQ ID NO:4 and FIG. 2b discloses SEQ ID NO:5.

DETAILED DESCRIPTION

Figure 1A:
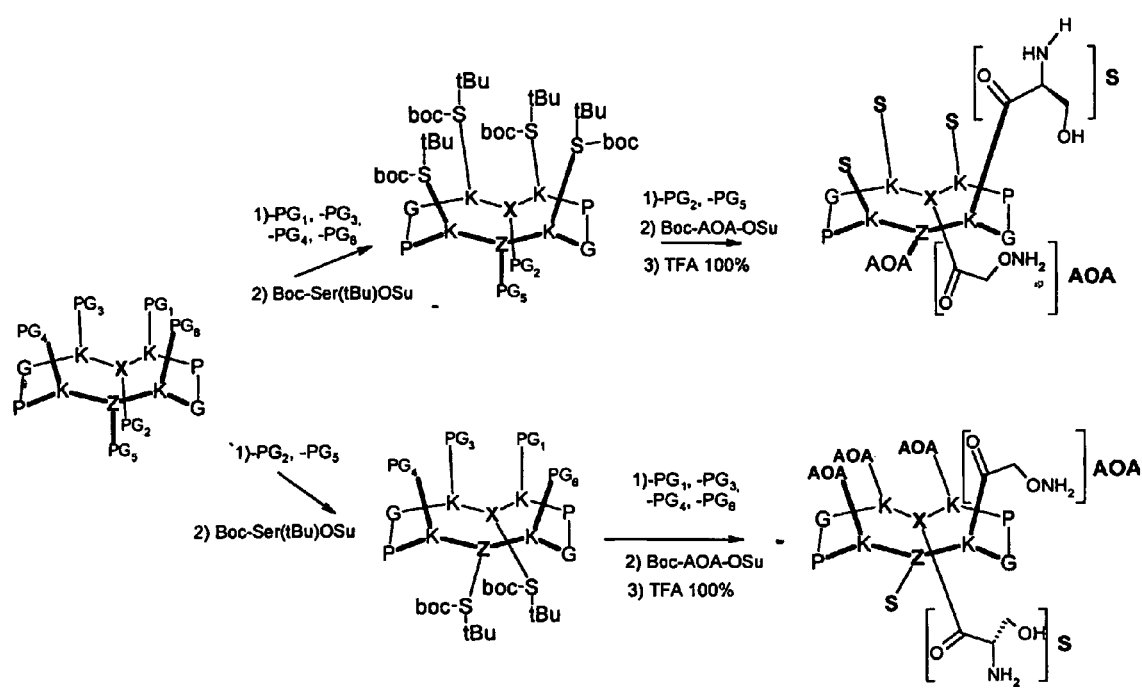
FIG. 1a is a diagram illustrating the preparation of cyclodecapeptides (SEQ ID NO: 5) according to aspects of the invention comprising on the one hand the serine precursor of the α-oxoaldehyde function on the upper face and the oxyamine function on the lower face, and on the other hand the oxyamine function on the upper face and the serine precursor of the α-oxoaldehyde on the lower face.

The invention relates to a method for preparing a grafted homodetic cyclopeptide forming a framework that defines two faces, a so-called "upper face" and a so-called "lower face," the two faces both being grafted, wherein a linear peptide is synthesized, the synthesis being performed from modified or unmodified amino acids, some of which carry orthogonal protective groups; an intramolecular cyclization of the resulting linear peptide is performed; some or all of the orthogonal protective groups are substituted with a protected precursor; at least one molecule of interest is grafted onto one and/or the other face of the framework via an oxime bond.

The present invention therefore concerns a method for preparing the molecular framework of a polyfunctional molecule, obtained in four steps: 1) synthesis of a linear peptide; 2) intramolecular cyclization of that linear peptide to yield a molecular framework; 3) functionalization of framework; 4) grafting of at least one molecule of interest onto one and/or the other face of that framework.

The amino acids used for the peptide synthesis are of any kind, including (D) series amino acids, (L) series amino acids, and any modified amino acid, the amino acids being natural or synthetic. Some of these amino acids are substituted with orthogonal protective groups. The orthogonal protective groups are chemical groups oriented perpendicularly with respect to the median plane of the framework; they mask the reactivity of an atom or group of atoms, and chemical elimination of them does not affect the other protective groups, of different kinds, present within the molecule. Their selection depends on the type of amino acid and the framework desired.

According to a first aspect of the invention, synthesis of the linear peptide, performed on the solid phase, is initiated with a glycine residue whose carboxyl function is anchored to a resin, and cyclization of the resulting linear peptide is performed in solution after release of the resin. The strategy of elongating a linear peptide of this kind is known (P. Dumy et al., *Tetrahedron Lett.* 1995, 36, 1244-1258). Initiating the synthesis with a glycine residue allows any risk of epimerization during the subsequent cyclization step to be eliminated. The glycine is preferably linked to the resin by its carboxyl function. Its alpha amino function is protected by a protective group that allows elongation of the peptide by synthesis. Following synthesis of the linear peptide, the alpha amino-terminated function of the peptide is released from the protective group during a first step, and the carboxy-terminated function is released from the resin during a second step of releasing the protected linear peptide; the side chains remain protected by their orthogonal protective group. The N- and C-terminated chemical functions released from the solubilized linear peptide react to form an intermolecular peptide bond during an intramolecular cyclization step performed in solution.

According to a second aspect, synthesis of the linear peptide and then cyclization thereof are performed entirely on the solid phase. Synthesis of the linear peptide is initiated with an amino acid residue whose side chain is anchored to a resin, leaving its carboxyl function unanchored. The alpha amino function and carboxyl function of this amino acid are each protected by a protective group, the two protective groups being orthogonal to one another.

Following synthesis of the linear peptide, the alpha amino-terminated and carboxy-terminated functions are selectively released from their respective protective groups, and the resulting linear peptide remains connected to the resin by the side chain of the first amino acid residue. The terminal chemical functions of the resulting linear peptide are then free to react among themselves and form an intramolecular cycle during an intramolecular cyclization step performed on the solid phase.

In this aspect, the method advantageously is entirely or partially automated on a peptide-synthesizing robot.

Advantageously, the cyclopeptide is constituted from 5, 10, or 14 amino acid residues, preferably 10 amino acids forming a cyclodecapeptide. The cyclopeptide cyclized exhibits at least one turn, preferably two turns. Some cyclopeptides according to the present invention exhibit a central symmetry.

According to another aspect, the cyclopeptide has 10 or 14 amino acid residues and forms two turns, each turn being constituted of an (L)Pro-(D)AA or (D)Pro-(L)AA combination, AA being an amino acid and preferably glycine, the two turns being separated by three and/or five amino acid residues.

The presence of the proline residue at the turn is justified by the fact that because of its cyclic structure, proline has a characteristic spatial configuration as compared to other amino acids. This characteristic imposes a conformational restriction on the peptide skeleton as compared to that assumed with amino acids other than proline or its derivatives. This restriction is, in particular, the cause of the bends in the secondary and supersecondary polypeptide structures.

The other amino acid residue of the turn, represented above by the symbol AA, is preferably an amino acid residue other than proline and having opposite stereochemistry, and very preferably the glycine residue.

The turns are separated by amino acid residues, preferably an odd number of amino acid residues, and very preferably three and/or five amino acid residues for a cyclodecapeptide and a cyclotetrapeptide, respectively.

The two-turn cyclopeptides having an even number of amino acid residues exhibit a median plane that defines the upper face and the lower face.

The three and/or five amino acid residues preferably each have a chemical function protected orthogonally by a protective group. The protective groups of the side chains of these amino acids are directed alternately to one side and the other of the median plane of the framework, and define the lower and upper face with respect to that plane.

These amino acid residues are preferably amino acid residues carrying chemical functions of the —NH2, —SH, or —COOH type. According to one aspect, these three or five amino acid residues are preferably amino acids having an amine side chain, and very preferably lysine.

According to another aspect, the orthogonal protective groups of the central amino acid residues are identical to one another, the orthogonal protective groups of the amino acid residues other than the central ones are identical to one another, the orthogonal protective groups of the central amino acid residues, on the one hand, and the orthogonal protective groups of the other amino acid residues, on the other hand, are different from one another.

According to a particular aspect, grafting of the framework is begun by substituting the orthogonal protective groups of the framework with a protected precursor of the oxyamine function or a masked precursor of the aldehyde function, in particular of the α-oxoaldehyde type or with a protected precursor of the thiol function, or with a label. According to one variant, the protected precursor of the thiol function is a dissymmetrical disulfide derivative of cysteine, in particular an Npys group (FIG. 1b).

According to another variant, this protected precursor is 2-oxyaminoacetic acid (OAA) protected on the nitrogen, or a seine derivative, precursor of the α-oxoaldehyde function, the amine and hydroxyl functions of which are protected, and deprotection of which followed by oxidative cleavage releases the aldehyde group, and preferably is Boc-Ser(tBu)OH.

According to aspect substitution of the orthogonal protective groups of the lower face with a label, preferably biotin or fluorescein, is performed. Then in a second step, the orthogonal protective groups of the upper face of the framework are substituted with a protected precursor of the oxyamine function or of the α-oxoaldehyde function. The oxyamine or α-oxoaldehyde function of the precursor, previously deprotected, is then reacted with a molecule of interest or an intermediate molecule carrying an α-oxoaldehyde or oxyamine function, respectively. Substitution of the lower face is conventional, whereas substitution of the upper face is chemoselective.

According to a second aspect, substitution of the orthogonal protective groups of the lower face of the framework with a protected precursor of the oxyamine function is performed. Then, in a second step, the orthogonal protective groups of the upper face of the cyclopeptide are substituted with a protected precursor of the α-oxoaldehyde function.

According to a third aspect, substitution of the orthogonal protective groups of the upper face of the framework with a protected precursor of the oxyamine function is performed. Then, in a second step, the orthogonal protective groups of the lower face of the cyclopeptide are substituted with a protected precursor of the α-oxoaldehyde function.

According to a fourth aspect, substitution of the orthogonal protective groups of one face of the framework with a protected precursor of the aldehyde or oxyamine function is performed, then substitution of the orthogonal protective groups of the other face of the framework with a protected precursor of the thiol function. Grafting of the molecules of interest is then performed by causing the complementary functional groups to react. Grafting of the molecules of interest carrying an aldehyde or oxyamine precursor onto the face of the framework carrying an oxyamine or aldehyde precursor, respectively, is performed. Then, the other face of the framework, in its free thiol form or in the form of activated dissymetrical disulfide, is reacted with a second molecule of interest carrying an activated dissymetrical disulfide or free thiol function, respectively. This second molecule is then attached to the framework via a disulfide link. The molecules of interest can be a peptide, a protein, an oligosaccharide, a nucleic acid, an organic molecule, an inorganic molecule (FIGS. 1b and 2b). Advantageously, this link can allow intracellular re-release of the molecule of interest so that it can perform its biological role.

As noted above, the active functions, in particular oxyamine or α-oxoaldehyde, of the precursors, previously deprotected, are reacted with one or several molecules of interest or with an intermediate molecule carrying a complementary function, such as α-oxoaldehyde or oxyamine respectively. Preferably the oxyamine function of the precursor located on the framework is reacted with a molecule of interest carrying an α-oxoaldehyde function, then the precursor of the α-oxoaldehyde function located on the framework is oxidized, and the reaction is continued by bringing the framework into contact with at least one molecule of interest, or an intermediate molecule, carrying an oxyamine function.

The intermediate molecule(s) on the one hand carry an oxyamine function capable of reacting with the α-oxoaldehyde function(s) located on the framework, and on the other hand carry a precursor of at least one α-oxoaldehyde function.

The molecule(s) of interest are identical to or different from one another.

Advantageously, the molecule of interest is a nucleic acid, a peptide, an oligosaccharide, or an organic molecule. Any molecule of therapeutic or diagnostic interest carrying an oxyamine or α-oxoaldehyde function can be grafted onto the framework.

According to a first variant, one face of the framework is grafted with peptides derived from the cyclo(RGDfK) (SEQ ID NO: 1) and cyclo(RGDyk) (SEQ ID NO: 2) ligands of integrin αvβ3 to direct the molecule toward tissues which express that receptor, and to modify biological effects for a therapeutic or diagnostic purpose;

a) If the purpose is therapeutic, the other face of the framework according to the invention is grafted with an apotogenic peptide of the (KLAKKLAK) (SEQ ID NO: 3) type, or a known organic molecule of the doxorobucin type, or an intracellularly toxic protein (ricin-A, galenin, . . . ).

b) If the purpose is in vitro and in vivo diagnosis, the other face of the framework is grafted with one or several chromophores, one or several biotins, one or several fluorophores, one or several radioemitters, or a precursor group (chemical or ligand).

According to a second variant, one face of the framework is grafted with carbohydrate derivatives to target their transmembrane receptor of the lectin type, in particular the mannose receptor, galactose receptor, asialo-protein receptor, GLUT glucose transporter, etc., for a therapeutic or diagnostic purpose;

c) If the purpose is therapeutic, the other face of the framework is grafted with one or several T-dependant epitopic peptides, one or several apotogenic peptides of the (KLAKKLAK) (SEQ ID NO: 3) type, or a known organic molecule of the doxorobucin type, or an intracellularly toxic protein (ricin-A, galenin, . . . ).

d) If the purpose is in vitro and in vivo diagnosis, the other face of the framework is grafted with one or several chromophores, one or several biotins, one or several fluorophores, one or several radioemitters, or a precursor group (chemical or ligand).

According to a third variant, one face of the framework is grafted with B-dependent epitopes of the peptide or carbohydrate type, more particularly tumor labels (Tn, sTn, Tf), one or several T-dependent epitopes (Th1 or Th2 peptides), and an immunoadjuvant, to evoke a cellular response for vaccination purposes.

According to a fourth variant, the faces are functionalized to impart recognition properties to them that are useful in miniaturized systems of the bio-chip type.

Advantageously, when synthesis and cyclization are performed in solid phases, the method is entirely or partially automated on a peptide-synthesizing robot.

The invention also relates to a grafted homodetic cyclopeptide, wherein it is obtained by the method according to the present invention.

The invention further relates to a therapeutic or diagnostic composition, wherein it comprises a grafted homodetic cyclopeptide obtained by the method.

The invention likewise concerns the use of a grafted homodetic cyclopeptide obtained by the method, or of a composition containing it, for production of a medication intended to treat cancer. The invention likewise concerns the use of a grafted homodetic cyclopeptide obtained by the method, or a composition containing it, as a tool for diagnosing cancer.

The invention likewise concerns the use of a grafted homodetic cyclopeptide obtained by the method, or a composition containing it, for the diagnosis and/or suppression of neoangiogenesis.

The invention likewise concerns the use of a grafted homodetic cyclopeptide obtained by the method, or a composition containing it, as a framework for functionalizing surfaces with the purpose of imparting to them recognition properties that are useful in miniaturized systems of the bio-chip type.

The use of a surface as a functional interface having recognition properties represents a strategy of choice for designing such systems, which is transferable to a large area of technology permitting micro- or nanoscale miniaturization, and well as connectivity, thereof.

On the one hand, functionalization of the host surface with one of the partners involved in recognition (probe: molecules, biomolecules, cells) is a key stage in achieving this molecular interaction at the interface between the surface and analyte. This addressing must be sufficiently gentle to preserve the integrity and the molecular properties of the probe, reproducible in order to be usable, and spatially controlled in order to allow concurrent detection of various targets. On the other hand, functionalization can also result in transduction of probe-target recognition into a measurable and quantifiable signal, allowing detection of the target. The great significance of this strategy is the absence of labeling of the target, allowing the approach to be generalized to any category of target.

In this context, the method allows one face of the framework to be used to address the surface, for example, by using thiol grafts or by electropolymerization using pyrrole-type pendants. The other face is used to graft the molecule of interest onto the surface. Advantageously, use of a precursor of the α-oxoaldehyde function protected by a photolabile group of the NVOC type allows spatially controlled addressing of the surface by a molecule of interest. The method is much more advantageous for functionalization of the surface than the procedures conventionally used.

Figure 1B:
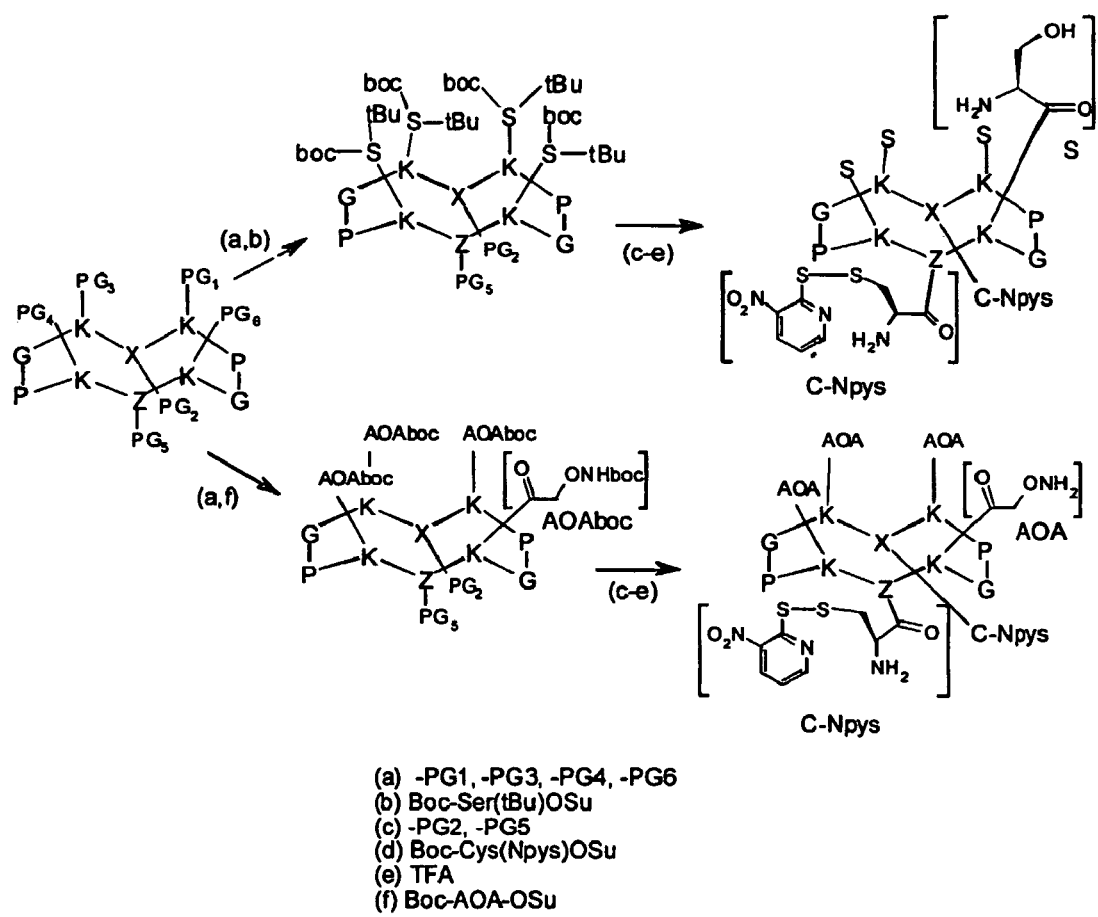
FIG. 1b is a diagram illustrating the preparation of cyclodecapeptides (SEQ ID NO: 5) according to aspects of the invention comprising either the serine precursor of the α-oxoaldehyde function or the α-oxoaldehyde on the upper face, and on the other hand the C-Npys function on the lower face.

According to a first aspect illustrated in FIG. 1a, substitution of the orthogonal protective groups PG of the lower face, or PG2 and PG5, is performed with a protected precursor of the α-oxoaldehyde function, preferably Boc-Ser(tBu)OH. In a second step, the orthogonal protective groups of the upper face of the framework (PG1, PG3, PG4, PG6) are substituted with a protected precursor of the oxyamine function, preferably Boc-OAA-OS. In a third step depicted in FIG. 2a, all the protective groups are removed, and the now-deprotected oxyamine function on the lower face proceeds to react in the presence of a first molecule of interest carrying an α-oxoaldehyde function. In a fourth step depicted in FIG. 2a, the seryl residues are oxidized to α-oxoaldehyde functions on the upper face. In a fifth step, the α-oxoaldehyde functions of the upper face are reacted with a second molecule of interest carrying an oxyamine function.

Figure 2A:
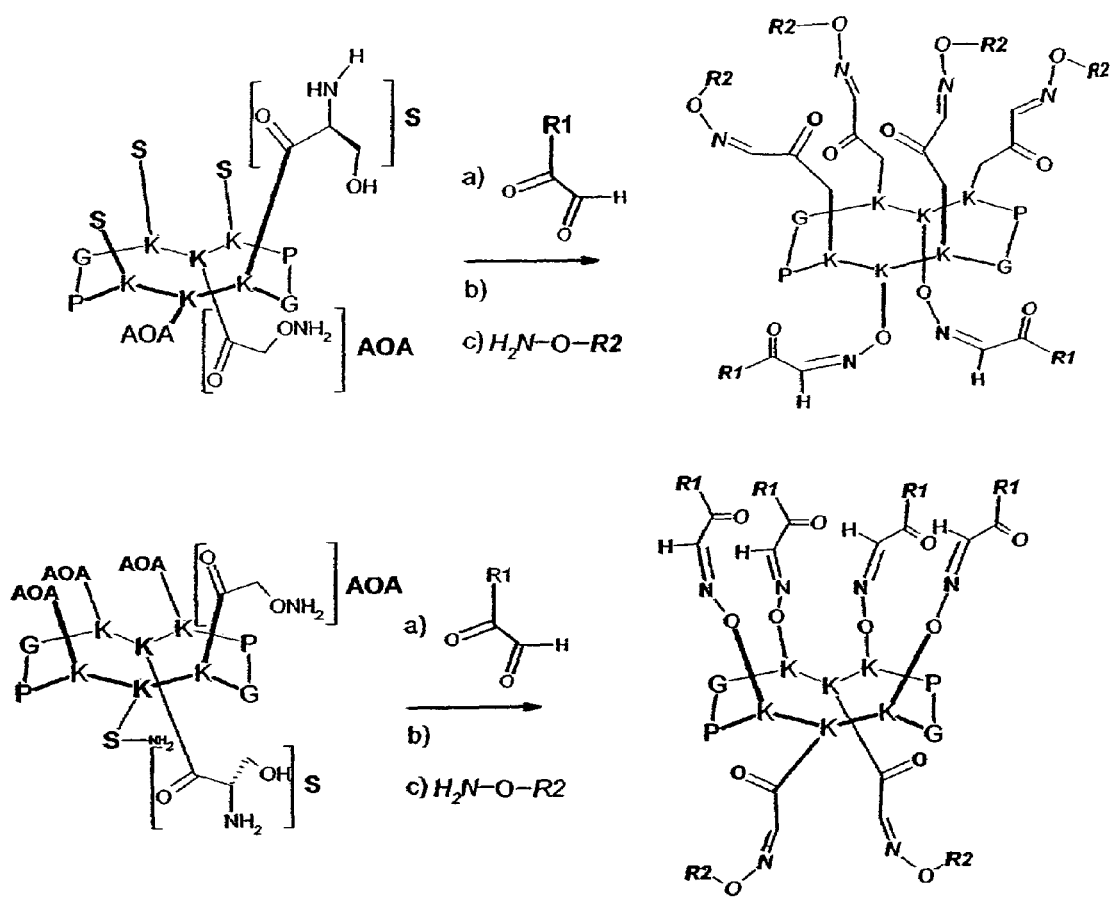
FIGS. 2a and 2b are diagrams illustrating the preparation of polyfunctional macromolecules by successive chemoselective assembly of biomolecules R1 and R2 using an oxime bond, on the one hand onto the lower and then upper face of the cyclodecepeptide, and on the other hand onto the upper and then lower face of the cyclodecapeptide.
Figure 2B:
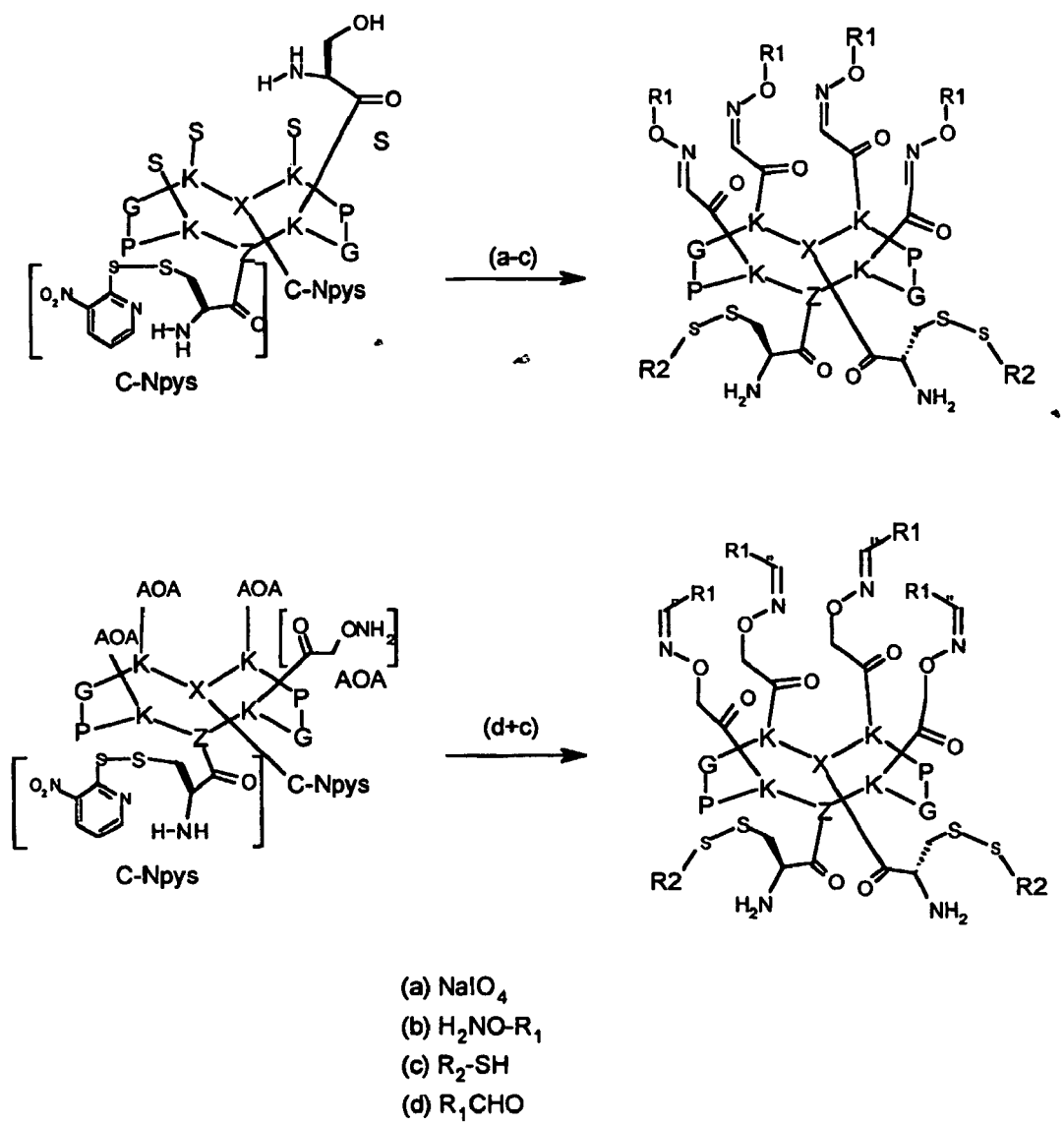
Figure 3:
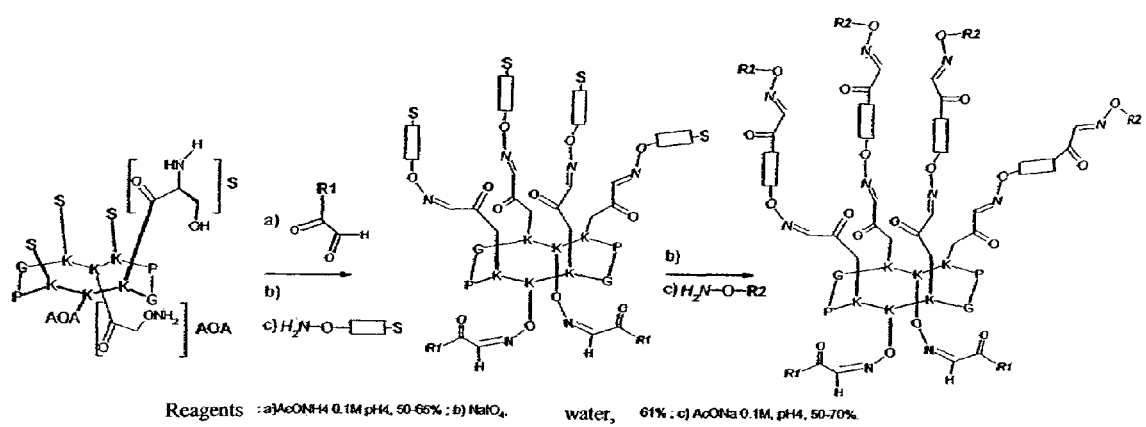
FIG. 3 is a diagram illustrating the synthesis of polyfunctional macromolecules by successive chemoselective assembly via an oxime bond, in which the R1 biomolecule is grafted onto one face of the cyclodecapeptide: in which four molecules comprising an oxyamin function and at least one serine precursor of the α-oxoaldehyde function are grafted onto the other face of the cyclopeptide (SEQ ID NO: 4); and in which lastly the R2 biomolecule is wafted after demasking of the α-oxoaldehyde functions.

According to the second aspect depicted in FIGS. 1a and 2a, the sequence of substituting the orthogonal protective groups and grafting the upper and lower faces is respectively reversed as compared to the first aspect. According to a particular aspect depicted in FIG. 3, the last molecule of interest grafted onto the framework via its oxyamine function, permitting it to be grafted onto the α-oxoaldehyde function(s) located on the framework, carries at least one precursor of an α-oxoaldehyde function. This allows the method to proceed by oxidizing this precursor to α-oxoaldehyde and reacting the latter with a molecule of interest exhibiting an oxyamine function, in order to create a supplementary oxime bond. This complementary step allows the construction of a modular system via iterative oxime coupling onto the framework, by demasking the α-oxoaldehyde function by successive oxidation.

Figure 4:
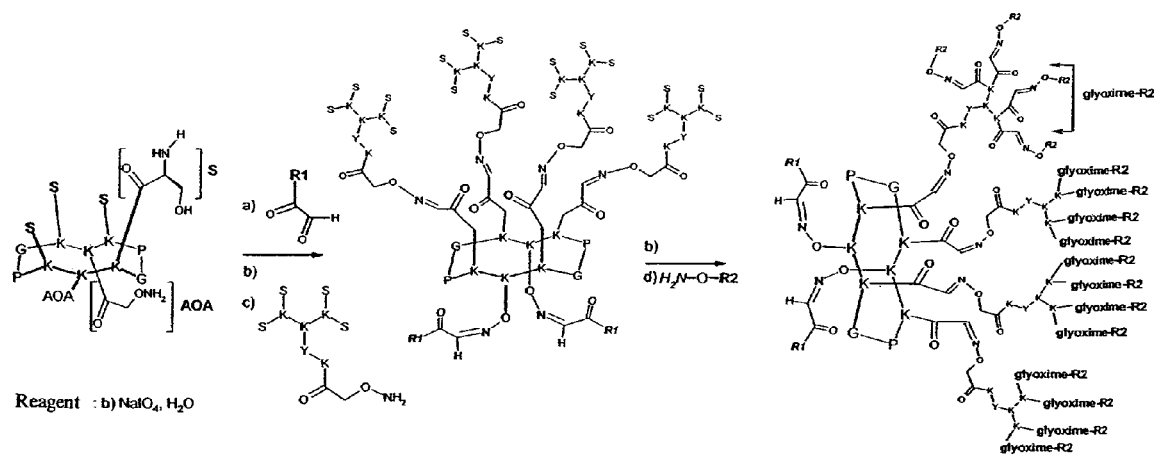
FIG. 4 is a diagram illustrating the synthesis of polyfunctional macromolecules by successive chemoselective assembly via an oxime bond, in which the R1 biomolecule is grafted onto one face of the cyclodecapeptide (SEQ ID NO: 4); in which four molecules comprising an oxyamine function and four serine precursors of the α-oxoaldehyde function are wafted onto the other face of the cyclopeptide; and in which lastly the R2 biomolecule is grafted after demasking of the α-oxoaldehyde functions.

As described by FIG. 4, this particular aspect advantageously allows an amplification of the number of molecules presented in situ by the framework in the case of a molecule of interest that, grafted onto the framework via its oxyamine function which allows it to be grafted onto the α-oxoaldehyde function(s) located on the framework, carries more than one precursor of an α-oxoaldehyde function.

EXAMPLE 1

A cyclopeptide forming a framework grafted on one face with peptides derived from cycle(RGDfK) (SEQ ID NO: 1) and/or cyclo(RGDyK) (SEQ ID NO: 2), which are ligands of integrin αVβ3.

The cyclo(RGDfK) (SEQ ID NO: 1) peptides recognize integrin αVβ3. This integrin is overexpressed on the cell surface of tumors or endothelial cells during tumoral neoangiogenesis. Grafting of this peptide onto one face of the framework enhances the ability of this peptide to be recognized by this integrin. In addition, the biological effects of this integrin, for example clustering, and endocytosis of the molecule, are triggered by the framework grafted in this fashion, while they are not triggered by the peptide alone.

1) Support for cell culture in vitro: Frameworks comprising a biotin group on one of their faces make it possible in general to functionalize that face with streptavidin by means of the strong biotin-streptavidin interaction. The other face of the framework can be functionalized with a molecule of interest, or unoccupied.

The use of frameworks comprising, for example, adhesion ligands such as cyclo(RGDfK) (SEQ ID NO: 1) allows the attachment of cells expressing the αVβ3 receptor and in vitro culture thereof. The compounds prove to be particularly effective with a low density of molecules adsorbed onto the surface.

Figure 5:
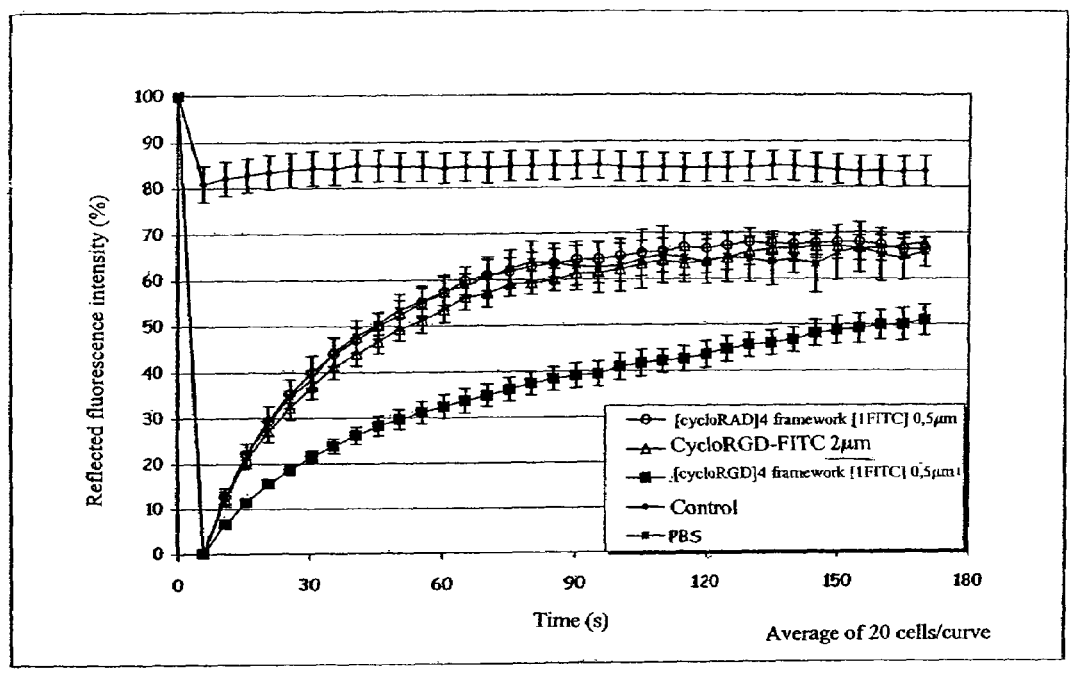
FIG. 5 depicts the fluorescence signal of the αVβ3 receptor, after immunolabeling (LM609-R-phycoerythrin), recorded as a function of time for various incubation conditions of living HEK cells (FRAP experiment). The delay observed with the multivalent RGD compound (solid squares) expresses a decrease in the mobility of the αVβ3 receptors that is characteristic of the clustering phenomenon, which is not observed under the other conditions.
Figure 6:
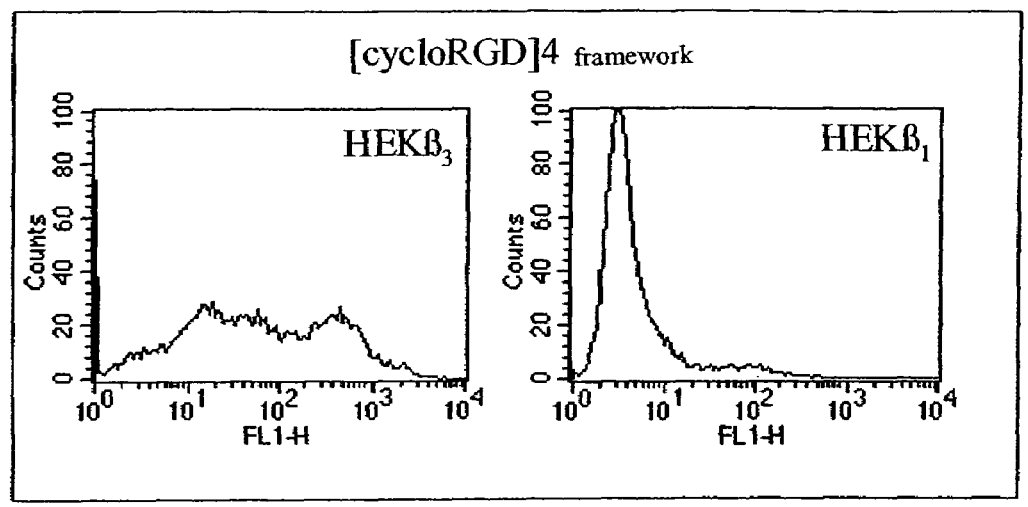
FIG. 6 depicts fluorescence histograms obtained by FACS after incubation of HEK cells with the multivalent RGD-fluorescein compound.

2) Inducing clustering of cell receptors (FIG. 5): Clustering of integrins at the surface of HEK293 cells that overexpress integrin β3 has been demonstrated by FRAP experiments. The living cells are placed in contact with an anti-$\alpha_v\beta_3$ antibody labeled with phycoerythrin (LM609-PE) and with various peptides. An area of the cell surface is then photobleached to measure the kinetics of the reappearance of the fluorescence signal in this area. This measurement reflects the speed at which integrin $\alpha_v\beta_3$ migrates into the plasma membrane of a living cell. If several integrin molecules are covered by the peptide, the "cluster" thus formed will then migrate less quickly than the native integrin $\alpha_v\beta_3$ which is smaller and freer. The results presented in FIG. 5 demonstrate that only the peptide obtained according to the invention is capable of inducing this kind of clustering of integrin $\alpha_v\beta_3$ at the surface of cells.

3) Active internalization of drugs or vectorized products: The same cells, placed in contact at 37° C. or 4° C. for 15 to 30 minutes with peptides previously labeled with fluorescein, are observed by confocal microscopy after immunolabeling of the early endosome vesicles (anti-Early Endosome 1A labeling, visualized in red).

The results obtained demonstrate that only the peptide obtained according to the invention can be visualized at 37° C. at the surface, at intercellular junctions, and in the interior of the cells. A significant proportion of the intracellular signal is co-localized with the EE1A label, demonstrating that at least a portion of the RAFT-RGD peptide is internalized by endocytosis. cRGD and RAFT-RGD peptides incubated under the same conditions are not detectable by immunofluorescence. This demonstrates their inability to become attached to their integrin target as effectively as the compound obtained according to the invention. If incubation of the peptides is performed at 4° C., only the extracellular label is observed with the peptide obtained according to the invention, confirming that internalization takes place by way of an active process.

4) Targeting vector for transferring biomolecules (DNA, peptides, proteins, PNA, oligonucleotides, siRNA): Only cells expressing integrin $\alpha_v\beta_3$ are recognized by the peptide obtained according to the invention. Incubation of HEK293 cells overexpressing either integrin β1 or β3 with the fluorescent peptide obtained according to the present invention demonstrates that the peptide attaches exclusively to the cells that overexpress the $\alpha_v\beta_3$ heterodimer. This property can be utilized to transport molecules of interest toward a target receptor.

5) Tumors expressing integrin $\alpha_v\beta_3$: The fluorescent peptide obtained according to the invention, injected intravenously into a tumor-carrying mouse, reveals under medical imaging that this peptide is found to accumulate strongly in the hypervascularized regions of the tumor.

6) Blood vessels: Our results obtained with fluorescent peptides obtained according to the invention demonstrate that the endothelium can be recognized by these molecules when intravenously injected. Other tissues, in particular the renal capsule, liver vessels, and spleen, have also been imaged using these molecules. Grafting of other ligands should allow augmentation of the signal obtained from the endothelium.

7) Enzymatic activity, in a clinical context or in vitro in a cell culture (esp. protease activity): Peptides containing a sequence specifically recognized by a protease can be grafted onto the framework. If a fluorescent molecule is grafted on upstream from the cleavage site, and a molecule that absorbs the fluorescence downstream from that site, the short distance between the two labels prevents any fluorescence emission. In the presence of the specific protease, however, the two fluorophores are dissociated and quantifiable light is therefore emitted. This procedure allows a determination of the protease concentration present in the compartment, tissue, or cell being observed.

The invention allows this system to be directed toward target tissues so that those regions can be specifically imaged.

Figure 7:
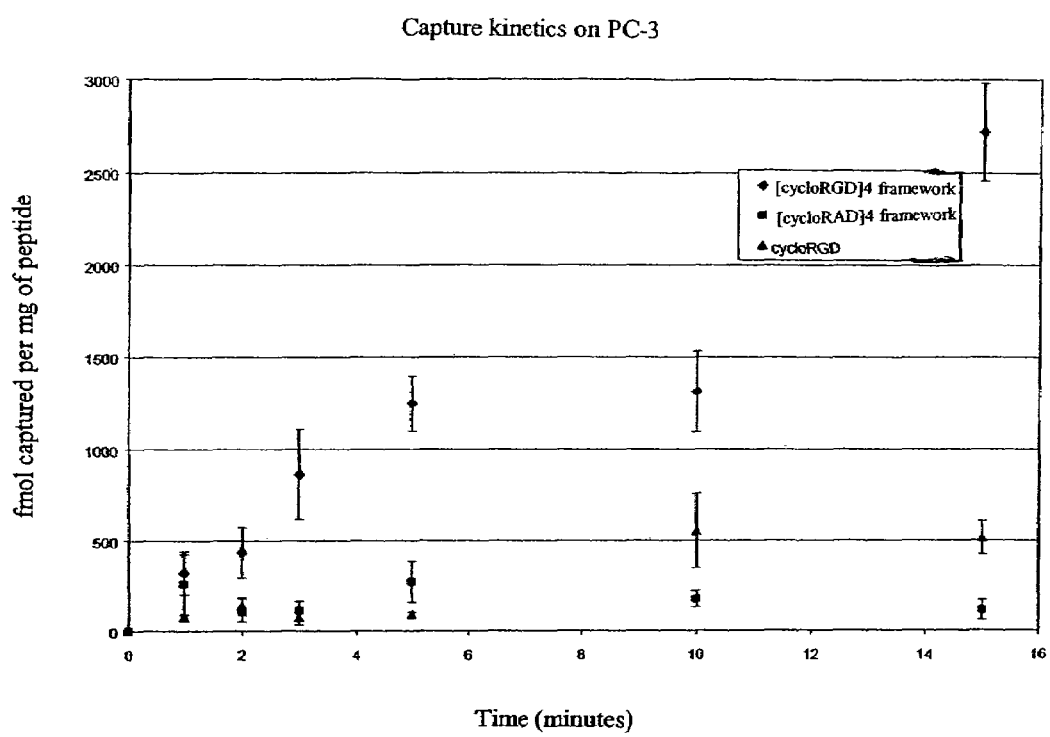
FIG. 7 compares the capture kinetics by PC3 cancer cells of the multivalent RGD compound assembled according to the invention (RAFT[cycloRGD]$_4$)—diamonds) with those of control molecules, by measuring the radioactivity of iodine-125.

8) Radiodetection of endothelial tissues during tumoral neoangiogenesis, or of tumors expressing integrin V3 (FIG. 7): Labeling with radioactive iodine-127 allows the detection of the molecule, and therefore of its binding with integrin on the cell surface followed by entry into the cytosol after endocytosis. The capture effect is dose-dependent in compounds. This effect has been measured in tumor cells (PC-3) and endothelial cells (HMVEC) that express integrin. Here again, only the grafted cyclopeptides according to the invention possess the effect observed, unlike the isolated ligand. This property allows the neoangiogenesis zones to be imaged by measuring radioactivity.

EXAMPLE 2

A cyclopeptide according to the invention forming a framework grafted on one face with B-dependent epitopes of the carbohydrate type, more particularly a tumor label (Tn, sTn, Tf), one or several T-dependent epitopes (Th1 or Th2 peptides), and an immunoadjuvant.

These substituents are selected to evoke a cellular response for vaccination purposes.

Sugars are known to be very important factors in numerous pathologies, particularly cancer (tumor label) or viral and bacterial infections. They are weakly immunogenic, however, which greatly limits their use in vaccine components for obvious therapeutic purposes. In addition, recognition of sugar units is mediated by a presentation in the form of bunches,which also limits their use. The invention allows the presentation of sugar units in the form of bunches, as well as chemical manipulation of them to produce epitopic combinations ultimately capable of evoking learning by the immune system to protect the organism from pathologies and infections involving those units.

The invention claimed is:

1. A grafted homodetic cyclopeptide combining both cell-targeting and therapeutic/diagnostic functions, the cyclopeptide forming a framework that defines a grafted upper face and a grafted lower face; wherein one face is grafted with at least one molecule of therapeutic or diagnostic interest, and the other is grafted with at least one recognition molecule of interest; said cyclopeptide being obtained by a process comprising:
   synthesizing a linear peptide from modified or unmodified amino acids, some of which carry orthogonal protective groups, whereby the linear peptide has a terminal glycine residue;
   intramolecularly cyclizing the resulting protected linear peptide through the terminal glycine residue;
   substituting some or all of orthogonal protective groups with a protected precursor suitable for grafting a molecule of interest; and
   grafting at least one molecule of therapeutic or diagnostic interest on one face of the cyclopeptide framework, and at least one recognition molecule of interest on the other face of the cyclopeptide framework;
   wherein at least one molecule of interest is grafted onto the upper or lower face of the framework via an oxime bond.

2. The grafted homodetic cyclopeptide as defined in claim 1, wherein at least one recognition molecule is a ligand of integrin αvβ3 comprising peptides derived from cyclo(L-Arg-L-Gly-L-Asp-D-Phe-L-Lys) (SEQ ID NO: 1) and/or cyclo(L-Arg-L-Gly-L-Asp-D-Tyr-L-Lys) (SEQ ID NO: 2), which are ligands of integrin, and the molecule of diagnostic interest is a KLAKKLAK (SEQ ID NO: 3) apotogenic peptide, a known therapeutic doxorobucin molecule, or a protein that is toxic at the intracellular level.

3. The grafted homodetic cyclopeptide as defined in claim 1, wherein at least one recognition molecule is a ligand of integrin αvβ3, comprising peptides derived from cyclo(L-Arg-L-Gly-L-Asp-D-Phe-L-Lys) (SEQ ID) NO: 1) and/or cyclo(L-Arg-L-Gly-L-Asp-D-Tyr-L-Lys) (SEQ ID NO: 2), which arc ligands of integrin, and the molecule of diagnostic interest is a chromophore, a biotin, a fluorophore, a radioemitter, or a precursor thereof.

4. The grafted homodetic cyclopeptide as defined in claim 1, wherein the recognition molecule is a carbohydrate derivative and the therapeutic molecule is one or several T-dependent epitipic peptides, one or several cytotoxic peptides, one or several therapeutic organic molecule(s), or a protein that is toxic at the intracellular level.

5. The grafted homodetic cyclopeptide as defined in claim 1, wherein the recognition molecule is a carbohydrate derivative and the diagnostic molecule of interest is one or several chromophore(s), one or several biotin(s), one or several fluorophore(s), one or several radioemitter(s), or a chemical precursor group or ligand.

6. The grafted homodetic cyclopeptide as defined in claim 1, grafted on one face with an immunoadjuvant and B-dependent epitopes comprising carbohydrates, or T-dependent epitopes.

7. A therapeutic or diagnostic composition, comprising a grafted homodetic cyclopeptide as defined in claim 1 and a pharmaceutically acceptable carrier.

8. A method of treating cancers expressing an αvβ3 integrin comprising administering to a patient in need thereof a therapeutically effective amount of a composition as defined in claim 7.

9. A method of treating cancers expressing an αvβ3 integrin comprising administering to a human patient in need thereof a therapeutically effective amount of a composition as defined in claim 7 for the suppression of neoangiogenesis.

10. A method for preparing a grafted homodetic cyclopeptide according to claim 1, comprising:
    synthesizing a linear peptide from modified or unmodified amino acids, some of which carry orthogonal protective groups, whereby the linear peptide has a terminal glycine residue;
    intramolecularly cyclizing the resulting protected linear peptide through the terminal glycine residue thereby producing a cyclopeptide framework;
    substituting some or all of the orthogonal protective groups with a protected precursor of an oxyamine function or a protected masked precursor of an aldehyde function which is suitable for grafting a molecule of interest via an oxime bond; and
    grafting at least one molecule of therapeutic or diagnostic interest on one face of the cyclopeptide, and at least one recognition molecule of interest on the other face of the cyclopeptide;
    wherein at least one molecule of therapeutic or diagnostic interest is grafted onto the upper or lower face of the framework via an oxime bond.

11. The method as defined in claim 10, wherein synthesizing the linear peptide is performed on a solid phase, whereby the synthesis is initiated from a glycine residue whose carboxyl function is anchored to a resin, and wherein the step of cyclizing the resulting linear peptide is performed in solution after release of the peptide from the resin.

12. The method as defined in claim 10, wherein synthesizing and cyclizing the linear peptide are performed entirely on solid phase.

13. The method as defined in claim 12, wherein synthesizing the linear peptide is initiated with an amino acid residue whose side chain is anchored to a resin.

14. The method as defined in claim 10, performed entirely or partially on an automated peptide-synthesizing robot.

15. The method as defined in claim 10, wherein the cyclopeptide is formed from 5, 10 or 14 amino acid residues.

16. The method as defined in claim 14, wherein the cyclopeptide has 10 or 14 amino acid residues and forms two turns, the two turns comprising an (L)Pro-(D)AA and/or (D)Pro-(L)AA combination, with AA being an amino acid the two turns being separated by three or five amino acid residues, respectively.

17. The method as defined in claim 15, wherein the three or five amino acid residues each have, on a side chain, a chemical function initially protected orthogonally by a protective group, the protective groups being directed alternately to one side and the other of a median plane of the framework, and defining a lower and upper face with respect to that plane.

18. The method as defined in claim 14, wherein the three or five amino acid residues are amino acid residues having an amine side chain.

19. The method as defined in claim 14, wherein the orthogonal protective groups of the central amino acid residues are identical to one another, the orthogonal protective groups of the other amino acid residues are identical to one another, and the orthogonal protective groups of the central amino acid residues and the orthogonal protective groups of the other amino acid residues are different from one another.

20. The method as defined in claim 10, wherein the protected precursor is protected 2-oxyaminoacetic acid (OAA).

21. The method as defined in claim 10, wherein the protected masked precursor is a serine residue.

22. The method as defined in claim 10, wherein the protected precursor is a precursor of the thiol function.

23. The method as defined in claim 10, further comprising: substituting the orthogonal protective groups of the lower face of the framework with a label, and substituting orthogonal protective groups of the upper face of the framework with a protected precursor of the oxyamine function or of the aldehyde function.

24. The method as defined in claim 10, further comprising: substituting the orthogonal protective groups of the lower face of the framework with a protected precursor of the oxyamine function, and substituting the orthogonal protective groups of the upper face of the framework with a protected masked precursor of the aldehyde function.

25. The method as defined in claim 10, further comprising: substituting the orthogonal protective groups of the upper face of the framework with a protected precursor of the oxyamine function, and substituting the orthogonal protective groups of the lower face of the framework with a protected masked precursor of the aldehyde function.

26. The method as defined in claim 10, wherein the oxyamine or aldehyde functions generated from the precursors are deprotected and reacted with one or several molecules of interest or with an intermediate molecule carrying an aldehyde or oxyamine function.

27. The method as defined in claim 26, wherein the molecule of interest is selected from the group consisting of nucleic acids, peptides, oligosaccharides, or organic molecules.

28. The method as defined in claim 27, wherein at least one molecule of interest is the cyclopentapeptide cyclo(L-Arg-L-Gly-L-Asp-D-Phe-L-Lys) (SEQ ID NO: 1).

29. The method as defined in claim 27, wherein the oxyamine function of the precursor located on the framework is reacted with at least one molecule of interest carrying an aldehyde function, and the precursor of the aldehyde function located on the framework is oxidized and the reaction is continued by bringing the framework into contact with a molecule of interest or an intermediate molecule carrying an oxyamine function.

30. The method as defined in claim 26, wherein the intermediate molecule carries an oxyamine function capable of reacting with the aldehyde function(s) located on the framework or carries a precursor of at least one aldehyde function.

31. The method as defined in claim 12, performed entirely or partially automated on a peptide-synthesizing robot.

* * * * *